United States Patent [19]

Tocco

[11] 4,098,891

[45] Jul. 4, 1978

[54] CERTAIN S-TRIAZINES AS LIPOGENESIS INHIBITORS

[75] Inventor: Dominick J. Tocco, Lansdale, Pa.

[73] Assignee: Shell Oil Company, Houston, Tex.

[21] Appl. No.: 842,714

[22] Filed: Oct. 17, 1977

[51] Int. Cl.$^2$ .................... A61K 31/535; A61K 31/53
[52] U.S. Cl. .................. 424/248.56; 424/249
[58] Field of Search ............................ 424/249, 248.56

[56] References Cited

PUBLICATIONS

Merckle–Chem. Abst. vol. 84 (1976) pp. 180, 302r.
Metz et al.–Chem. Abst. vol. 84 (1976) p. 83991g.

*Primary Examiner*—Sam Rosen

[57] ABSTRACT s-Triazines substituted by one trichloromethyl moiety, and by two of certain amino moieties, inhibit lipogenesis in mammals.

1 Claim, No Drawings

CERTAIN S-TRIAZINES AS LIPOGENESIS INHIBITORS

DESCRIPTION OF THE INVENTION

It has been found that lipogenesis in mammals is inhibited by certain s-triazines which are described by the formula

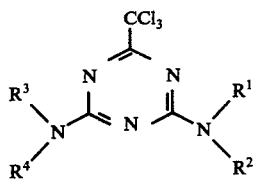

wherein
$R^3$ is hydrogen, alkyl, hydroxyalkyl, alkoxyalkyl, alkanoyloxyalkyl, dialkylcarbamoyloxyalkyl, carboxyalkyl, carboxyalkanoyloxyalkyl, or alkoxycarbonylalkanoyloxyalkyl, morpholinoalkyl or morpholinocarbonylalkyl;
$R^4$ is a moiety represented by $R^3$, other than hydrogen;
$R^3$ and $R^4$ together with the indicated nitrogen atom represent

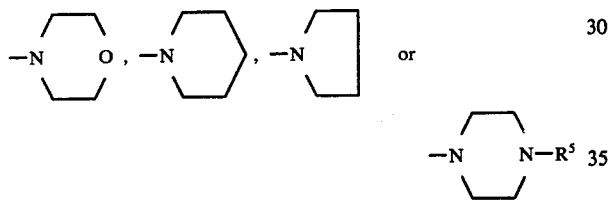

wherein
$R^5$ is hydrogen, alkyl, hydroxyalkyl, alkanoyl, carboxyalkanoyl, mono- or di(hydroxyalkyl)carbamoyl, carbanilino, or carboxyalkanoyloxyalkyl;
$R^1$ is hydrogen or alkyl;
$R^2$ is a moiety represented by $R^3$, other than hydrogen.

In these triazines, each alkyl moiety suitably is straight-chain or branched-chain in configuration and contains from one to four carbon atoms, while each alkylene moiety (as in a "hydroxyalkyl" moiety) suitably can contain from two to four carbon atoms, can be straight-chain or branched-chain in configuration, and the indicated substituent moieties can be substituted on any carbon atom thereof other than the alpha carbon atom—i.e., the carbon atom bonded to the indicated nitrogen atom.

Examples of these triazines are the following individual species, wherein $R^3$, $R^4$ (or $R^3 + R^4$ together), $R^1$ and $R^2$ are, respectively, as indicated:

| Compound No. | $R^3$; $R^4$; or ($R^3 + R^4$); $R^1$; $R^2$ |
|---|---|
| 1 | (morpholino); hydrogen; 2-hydroxyethyl. |
| 2 | (morpholino); hydrogen; 3-hydroxypropyl. |
| 3 | (morpholino); hydrogen; 2-acetoxyethyl. |
| 4 | (morpholino); hydrogen; 2-hydroxypropyl. |
| 5 | hydrogen; 3-methoxypropyl; hydrogen; 2-hydroxyethyl. |
| 6 | 2-hydroxyethyl; 2-hydroxyethyl; hydrogen; 3-isopropoxypropyl. |
| 7 | (morpholino); methyl; 2-hydroxyethyl. |
| 8 | hydrogen; 2-hydroxyethyl; methyl; 2-hydroxyethyl. |
| 9 | (morpholino); hydrogen; 2-(dimethylcarbamoyloxy)ethyl. |
| 10 | (morpholino); hydrogen; 2-(3-(methoxycarbonyl)propionyloxy)ethyl. |
| 11 | (4-acetylpiperazino); hydrogen; 2-hydroxypropyl. |
| 12 | (4-(phenylcarbamoyl)piperazino); hydrogen; 2-hydroxypropyl. |
| 13 | (4-(3-carboxypropionyl)-piperazino); hydrogen; 2-hydroxypropyl. |
| 14 | (morpholino); hydrogen; 2-acetamidoethyl. |
| 15 | (morpholino); hydrogen; 2-carboxyethyl. |
| 16 | hydrogen; 3-morpholino-carboxyethyl; hydrogen; ethyl. |
| 17 | hydrogen; 3-morpholinopropyl; hydrogen; 1,1-dimethyl-2-hydroxyethyl. |
| 18 | (pyrrolidino); hydrogen; 2-hydroxyethyl. |
| 19 | (4-(2-hydroxyethyl)carbamoyl)-piperazino); hydrogen; 2-hydroxyethyl. |
| 20 | (4-methylpiperazino); hydrogen; 2-hydroxyethyl. |
| 21 | (piperazino); hydrogen; 2-hydroxyethyl. |
| 22 | (piperazino); hydrogen; 2-hydroxypropyl. |
| 23 | (morpholino); hydrogen; 1,1-dimethyl-2-hydroxyethyl. |
| 24 | (4-methylpiperazino); hydrogen; 2-hydroxypropyl. |
| 25 | (4-((2-hydroxyethyl)carbamoyl)-piperazino); hydrogen; 2-hydroxyethyl. |
| 26 | (4-methylpiperazino); hydrogen; 2-(3-carboxypropionyloxy)ethyl. |
| 27 | (morpholino); hydrogen; 2-(3-carboxypropionyloxy)ethyl. |
| 28 | (morpholino); hydrogen; 2-methyl-2-(3-carboxypropionyloxy)ethyl. |
| 29 | (morpholino); hydrogen; 2-methyl-2-(4-carboxybutyryloxy)ethyl. |
| 30 | (4-(2-hydroxyethyl)piperazino); hydrogen; ethyl. |
| 31 | (4-(2-(3-carboxypropionyloxy)-ethyl)piperazino); hydrogen; ethyl. |
| 32 | (piperidino); hydrogen; 2-hydroxyethyl. |
| 33 | (piperidino); hydrogen; ethyl. |

These triazines are known compounds, many being specifically disclosed in, and methods for preparation of all of them being disclosed in, U.S. Pat. Nos. 3,462,430 and 3,549,755.

The compounds of formula I have been found to inhibit lipogenesis in tissues of mammals. The manner in which they cause this effect is not known with certainty; it is believed that they interfere with the synthesis of fatty acids in the tissues. Their effectiveness for this purpose has been ascertained in one series of tests by immersing samples of swine adipose tissue in a liquid medium containing radioactive glucose and the test chemical, for a period of time, then isolating the lipid from the treated tissue and determining the up-take of the radioactive carbon by means of scintillation counting techniques. These tests were conducted in swine adipose tissue because in swine, the primary site of lipogenesis—i.e., fatty acid synthesis—appears to be adipose tissue.

Described in more detail, the tests were conducted according to the following general procedure:

150 Milligrams of slices of swine adipose tissue were incubated at 37° C for 2 hours with shaking in 3 milliliters of Krebs-Ringer bicarbonate solution containing one half the normal calcium ion concentration, 60 micromoles of glucose, 0.5 micro-Curie of glucose-U$^{14}$C, 300 microunits of insulin, and 5% dimethyl sulfoxide (DMSO). The test compounds were added as suspensions or solutions in DMSO and were present at a concentration of 100 micrograms per milliliter of the incubation mixture.

The incubation was terminated by addition of 0.25 milliliter of 1 N sulfuric acid. The resulting mixture was extracted with a total of 25 milliliters of chloroform:methanol (2:1, v/v). The extracts were washed according to Folch et al. (J. Biol. Chem., 226, 497–509, (1957)), air dried, and counted in a liquid scintillation counter with 15 milliliters of counting fluid (two parts toluene containing 0.4% w/v New England Nuclear Omnifluor; 1 part Triton X-100. The tests were conducted in triplicate and were accompanied by control tests in which all ingredients, proportions and conditions were the same except that no test compound was included. From the data obtained were calculated the percent inhibition of lipid synthesis by the test compound in each case. The data obtained from the tests are set out in Table 1, as the percent inhibition of lipogenesis compared to the results obtained in the control tests wherein only the test compound was omitted.

TABLE I

| Compound No. | Percent Inhibition |
|---|---|
| 1 | 63 |
| 2 | 59 |
| 3 | 33 |
| 4 | 44 |
| 5 | 44 |
| 6 | 62 |
| 7 | 32 |
| 8 | 58 |
| 9 | 65 |
| 10 | 43 |
| 11 | 72 |
| 12 | 29 |
| 13 | 21 |
| 14 | 66 |
| 15 | 44 |
| 16 | 38 |
| 17 | 43 |
| 18 | 63 |
| 19 | 75 |
| 20 | 27 |

The effect of compound 1 on inhibition of lipogenesis in swine was confirmed by an in vivo test in which Compound 1 was included in the feed given to young, growing pigs for seven days, at a dosage of approximately 50 milligrams of Compound 1 per kilogram of the pig's body weight per day. Adipose tissue biopsy samples were taken at days 0, 6, 7 and 13 (one week off the drug) and the effect of the test compound on lipogenesis was determined using tissue slices prepared from the biopsy samples, by the procedure used in the in vitro tests. Statistical analysis of the results indicated that at day 13 Compound 1 had significantly reduced lipogenesis. No symptom of toxicity due to the test compound was noted.

The effect of Compounds 1, 15, 19, 20, 21, 22 and 33 on rats was determined by a modification of the method of D. D. Feller, J. Biol. Chem., 206, 171 (1954): whole epididymal fat pads from 110–150 gram Sprague-Dawley rats were incubated in 4 milliliters of Krebs-Ringer bicarbonate buffer for 30 minutes in an atmosphere of 95% $O_2$–5% $CO_2$. At the end of the 30 minute period 1 milliliter of Krebs-Ringer bicarbonate buffer containing 8.2 micromoles of acetate (0.1 microcuries of acetate-1-$^{14}$C), 55.0 micromoles of glucose and 50.0 micromoles of succinic acid was added to the incubating mixture and the incubation was continued for 60 minutes more. Test compounds were dissolved in dimethyl sulfoxide (DMSO) and added to the incubating mixture with the fat pad. The final concentration of DMSO in most of the experiments was 0.2% and did not effect the incorporation of acetate-1-$^{14}$C into fat. The concentration of the test compound in the liquid medium was $10^{-4}$M. The incubation was carried out with paired fat pads; the contralateral fat pad from the same rat served as the untreated control.

After incubation, the fat pads were washed in two 5 milliliter aliquots of normal saline and extracted twice with 20 milliliters of chloroform:methanol (2:1) by vigorous shaking for 60 minutes. The extracts were combined and brought to volume with fresh organic solvent in a 50 milliliter volumetric flask containing 1 milliliter of 3N hydrochloric acid. A 5 milliliter aliquot of this mixture was transferred into a 20 milliliter scintillator vial and evaporated to dryness (50° C) to remove traces of acetic acid. To the vials were added 17 ml of scintillator solution consisting of 0.3% diphenyloxazole and 0.01% of 1,4-bis(2,5-phenyloxazolyl)benzene in a solvent of 23% ethanol in toluene. Radioactivity was measured by liquid scintillation counting.

Table II indicates the percent inhibition of incorporation of the acetate into long chain fatty acids—a measure of inhibition of lipogenesis.

TABLE II

| Compound No. | Percent Inhibition |
|---|---|
| 1 | 57 |
| 15 | 29 |
| 19 | 44 |
| 20 | 56 |
| 21 | 65 |
| 22 | 30 |
| 33 | 31 |

Compound 13 also was tested by this procedure and was found not to inhibit acetate incorporation.

The effect of Compound 1 on rats was confirmed by a series of tests in which Compound 1 was included on the diet of rats, and it was found that on sacrifice of the rats and weighing their fat pads, lipogenesis had been inhibited to a significant extent, compared to the control rats.

The triazines of formula I can be used to control lipogenesis in mammals such as, for example, pets, animals in a zoo, livestock, furbearing animals and domestic animals, including, but not limited to dogs, cats, mink, sheep, goats, swine, cattle, horses, mules and donkeys. The effect is obtained by administering an effective amount of one or a mixture of two or more of the triazines orally or parenterally to the animal. They may be adminstered as such, or as an active ingredient of a conventional pharmaceutical formulation. They may be administered orally by any convenient means. Thus, they may be orally administered as a drench, by intubation, in the animal's food and water, in a food supplement or in a formulation expressly designed for administration of the drug. Suitable formulations include solutions, suspensions, dispersions, emulsions, tablets, boluses, powders, granules, capsules, syrups and elixirs. For parenteral administration, they may be in the form of a solution, suspension, dispersion or emulsion. They can be administered in the form of an implant or other controlled sustained release formulation. Inert carriers, such as one or more of water, edible oil, gelatin, lactose, starch, magnesium stearate, talc or vegetable gum can be used. The dosage of the triazine needed to inhibit lipogenesis will depend upon the particular triazine used, and the particular animal being treated. However, in general, satisfactory results are obtained when the triazines are administered in a dosage of from about 1 to about 500 milligrams per kilogram of the animal's body weight. The triazine can be administered in a single dose or in a series of doses in the same day, or over a period of days. For any particular animal, a specific dosage regimen should be adjusted according to the individual need, the particular triazine(s) used as the inhibitor, and the professional judgment of the person administering or supervising the administration of the inhibitor. It is to be understood that the dosages set forth herein are exemplary only, and that they do not, to any extent, limit the scope or practice of the invention.

I claim:

1. A method of inhibiting lipogenesis in mammals which comprises administering, to a mammal in need of such treatment, an effective amount of a triazine of the formula

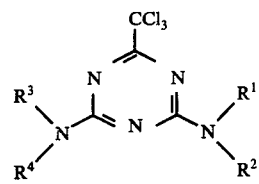

wherein
$R^3$ is hydrogen, alkyl, hydroxylalkyl, alkoxylalkyl, alkanoyloxyalkyl, dialkylcarbamoyloxyalkyl, carboxyalkyl, carboxyalkanoyloxyalkyl, or alkoxycarbonylalkanoyloxyalkyl, morpholinoalkyl or morpholinocarbonylalkyl;
$R^4$ is a moiety represented by $R^3$, other than hydrogen;
$R^3$ and $R^4$ together with the indicated nitrogen atom represent

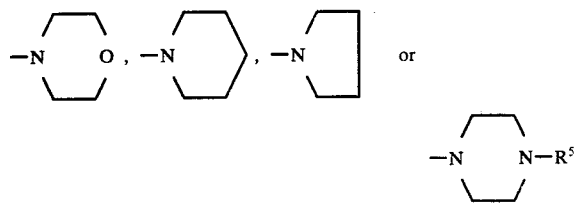

where
$R^5$ is hydrogen, alkyl, hydroxyalkyl, alkanoyl, carboxyalkanoyl, mono- or di(hydroxyalkyl)carbamoyl, carbanilino, or carboxyalkanoyloxyalkyl;
$R^1$ is hydrogen or alkyl;
$R^2$ is a moiety represented by $R^3$, other than hydrogen.

* * * * *